(12) United States Patent
Tang

(10) Patent No.: US 6,876,718 B2
(45) Date of Patent: Apr. 5, 2005

(54) SCATTER CORRECTION METHODS AND APPARATUS

(75) Inventor: Xiangyang Tang, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 105 days.

(21) Appl. No.: 10/608,460

(22) Filed: Jun. 27, 2003

(65) Prior Publication Data

US 2004/0264629 A1 Dec. 30, 2004

(51) Int. Cl.$^7$ ................................................ A61B 6/03
(52) U.S. Cl. ................................ 378/7; 378/4; 378/901
(58) Field of Search ............................... 378/4, 7, 8, 15, 378/19, 901

(56) References Cited

U.S. PATENT DOCUMENTS

| | | |
|---|---|---|
| 5,051,598 A | 9/1991 | Ashton et al. |
| 5,128,864 A | 7/1992 | Waggener et al. |
| 5,293,312 A | 3/1994 | Waggener |
| 5,307,264 A | 4/1994 | Waggener et al. |
| 5,351,203 A | 9/1994 | Hoffman et al. |
| 5,771,269 A | 6/1998 | Chao |
| 5,774,519 A | 6/1998 | Lindstrom et al. |
| 5,813,985 A | 9/1998 | Carroll |
| 5,960,058 A | 9/1999 | Baba et al. |
| 5,999,836 A | 12/1999 | Nelson et al. |
| 6,175,609 B1 | 1/2001 | Edic et al. |
| 6,216,540 B1 | 4/2001 | Nelson et al. |
| 6,369,389 B1 | 4/2002 | Berlad et al. |
| 6,399,951 B1 | 6/2002 | Paulus et al. |
| 6,408,049 B1 | 6/2002 | Edic et al. |
| 6,480,565 B1 | 11/2002 | Ning |
| 6,490,476 B1 | 12/2002 | Townsend et al. |
| 6,504,892 B1 | 1/2003 | Ning |
| 6,507,633 B1 | 1/2003 | Elbakri et al. |
| 6,618,466 B1 * | 9/2003 | Ning ............................ 378/62 |
| 2004/0081273 A1 * | 4/2004 | Ning ............................ 378/37 |

OTHER PUBLICATIONS

Ruola Ning, Xiangyang Tang and D.L. Conover, *X-Ray Scatter Suppression Algorithm for Cone Beam Volume CT*, Department of Radiology and Electrical & Computer Engineering, Department of Radiology, University of Rochester, Rochester, NY 14642, 8 pages.

Yifang Zhou, Tarun Mathur and Sabee Molloi, *Scatter and veiling glare estimation based on sampled primary intensity*, Department of Radiological Sciences, University of Calfornia, Irvine, CA 92697, Med. Phys. 26 (11), Nov. 1999, 1999 Am. Assoc. Phys Med., 10 pages.

* cited by examiner

*Primary Examiner*—David V Bruce
(74) *Attorney, Agent, or Firm*—Carl B. Horton, Esq.; Armstrong Teasdale LLP

(57) ABSTRACT

A method is provided which includes scanning an object with a cone beam volumetric computed tomography (CBVCT) system with a beam pass array positioned between an x-ray source of the CBVCT system and the object to acquire scatter data, scanning the object with the CBVCT system without the beam pass array positioned between the x-ray source and the object to acquire image data, and correcting the image data using the scatter data.

21 Claims, 2 Drawing Sheets

“SCATTER CORRECTION METHODS AND APPARATUS”

BACKGROUND OF THE INVENTION

This invention relates generally to computed tomography and more particularly to cone beam volumetric computed tomography.

An interference caused by x-ray scatter can undermine CT image quality and the validity of CT-based diagnostic imaging. In a single-row fan beam (FB) CT, the x-ray scatter is substantially reduced or almost eliminated through (1) shutting the aperture of a x-ray source collimator to a slit as the severity of x-ray scatter is proportional to the area illuminated by an x-ray beam, and (2) utilization of a detector collimator, which is cylindrically symmetric and focus at the focal spot of the x-ray source, to shield scattered x-ray photons but pass primary x-ray ones as much as possible. In a contemporary multi-row (up to 16) FB CT, those two measures are still being employed successfully to combat x-ray scatter interference. Hereinafter, both the single-row FB CT and multi-row FB CT are called FB CT. However, with a significant increment in row number, e.g., above 64, of a x-ray detector in cone beam (CB) volumetric CT, the techniques mentioned above will not work as well as their counterparts in FB CT, because (a) the aperture of x-ray source collimator is typically opened relatively wide in CB volumetric CT, and (b) the grid ratio of cylindrically symmetric detector collimator in volumetric CB CT can no longer be as high as that of their counterparts in FB CT, since an x-ray beam is intrinsically in sphere symmetry, and the uniformity of dynamic quantum efficiency (DQE) of an x-ray detector will be compromised by a cylindrically symmetric detector collimator if the grid ratio is as high as those in FB CT.

BRIEF DESCRIPTION OF THE INVENTION

In one aspect a method is provided. The method includes scanning an object with a cone beam volumetric computed tomography (CBVCT) system with a beam pass array positioned between an x-ray source of the CBVCT system and the object to acquire scatter data, scanning the object with the CBVCT system without the beam pass array positioned between the x-ray source and the object to acquire image data, and correcting the image data using the scatter data.

In another aspect, a cone beam volumetric computed tomography system is provided. The cone beam volumetric computed tomography system includes an x-ray source, a detector positioned to receive x-rays emitted from the source, and a beam pass array removably positioned between the source and the detector.

In a further aspect, a computer readable medium encoded with a program is provided. The computer readable medium is configured to instruct a computer to receive scatter data from a cone beam scan of an object with a beam pass array present, receive image data from a cone beam scan the object without the beam pass array present; and correct the image data using the scatter data.

DETAILED DESCRIPTION OF THE INVENTION

Figure 1:
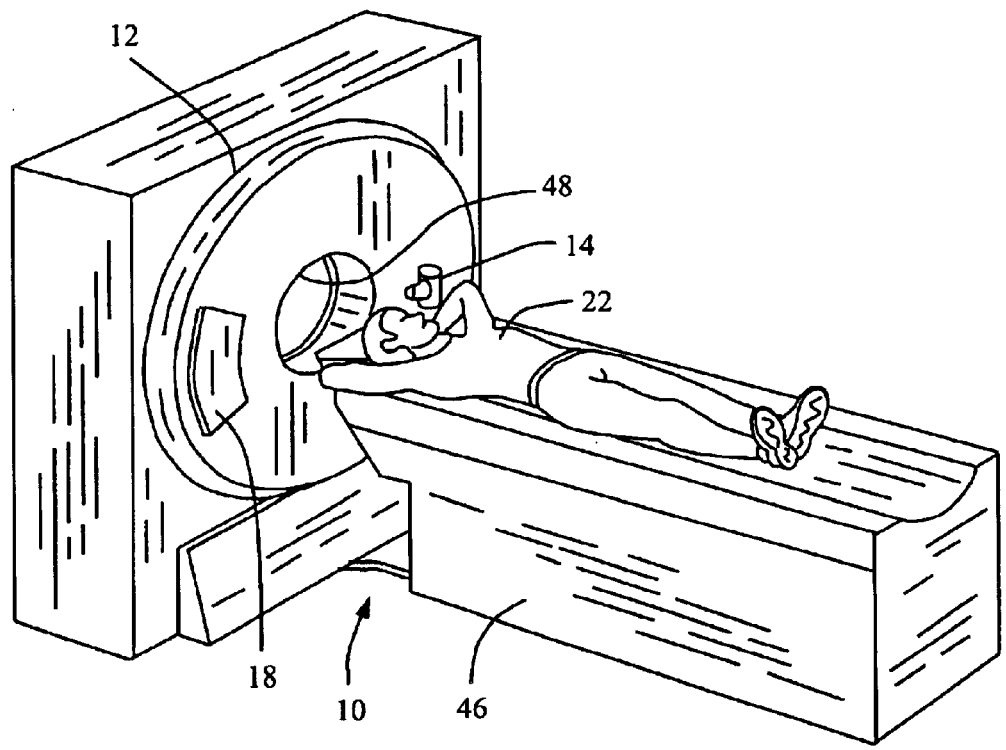
FIG. 1 is a pictorial view of a CT imaging system.

Apparatus and methods based upon x-ray scatter intensity sampling and image sequence processing are herein described which combat x-ray scatter interference in CB volumetric CT. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two dimensional slice taken through the object.

To further improve the performance of the CT system, multi-slice CT systems are built. In such systems, multiple projections are acquired simultaneously with multiple detector rows. For example, by extending the x-ray width in the z-axis forming a cone beam, cone beam helical scans are performed. Similar to the case of helical scan, weighting functions are applied to the projection data prior to the filtered backprojection process.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
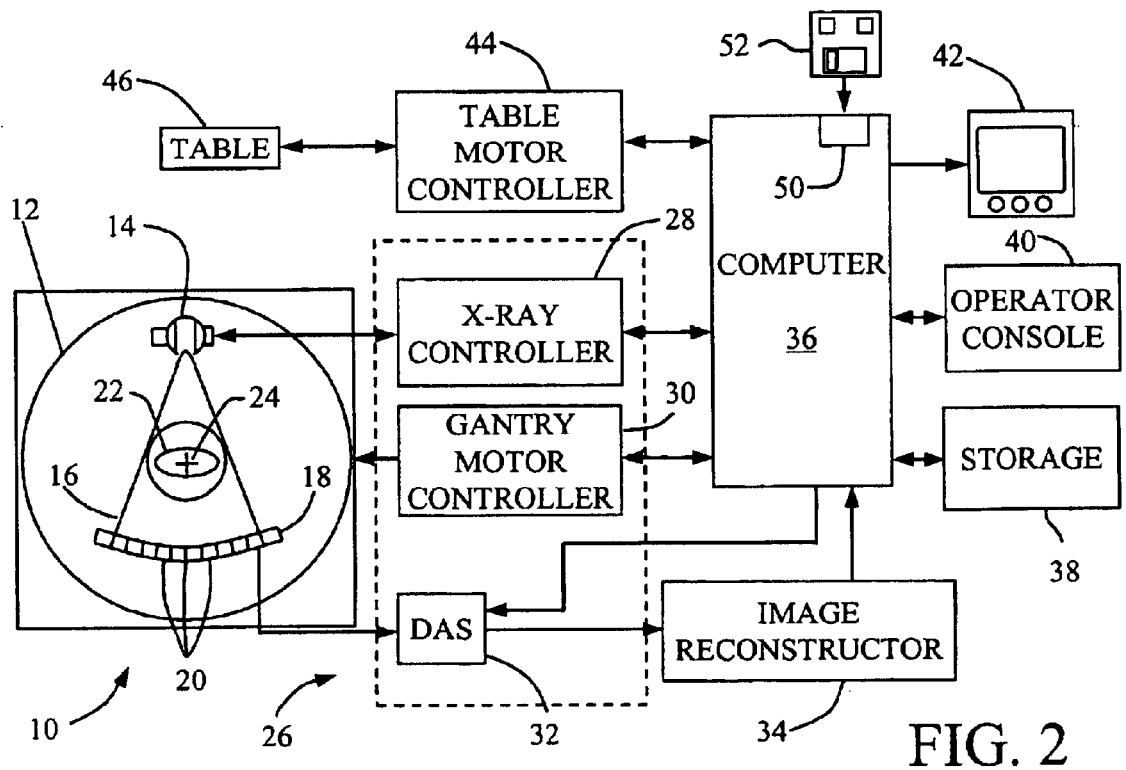
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan to enable cone beam helical scans and therefore, system 10 is sometimes herein referred to as a cone beam volumetric computed tomography (CBVCT) system.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Is has been well recognized that an x-ray projection image $I_t(x,y)$ consists of a primary image $I_p(x,y)$ formed by x-ray photons emanating from an x-ray source and a secondary image $I_s(x,y)$ by scattered x-ray photons, $$I_t(x,y)=I_p(x,y)+I_s(x,y) \quad (1)$$

and $I_s(x,y)$ can be further considered as a spatial low-pass filtering of $I_p(x,y)$, $$I_s(x,y)=LPF[I_p(x,y)] \quad (2)$$

where LPF represents the spatial low-pass filtering. This means that the spatial variation of $I_s(x,y)$ is much lower than that of $I_p(x,y)$. Hence, it is possible to reconstruct $I_s(x,y)$ from its samples measured at a sparse lattice.

Figure 3:
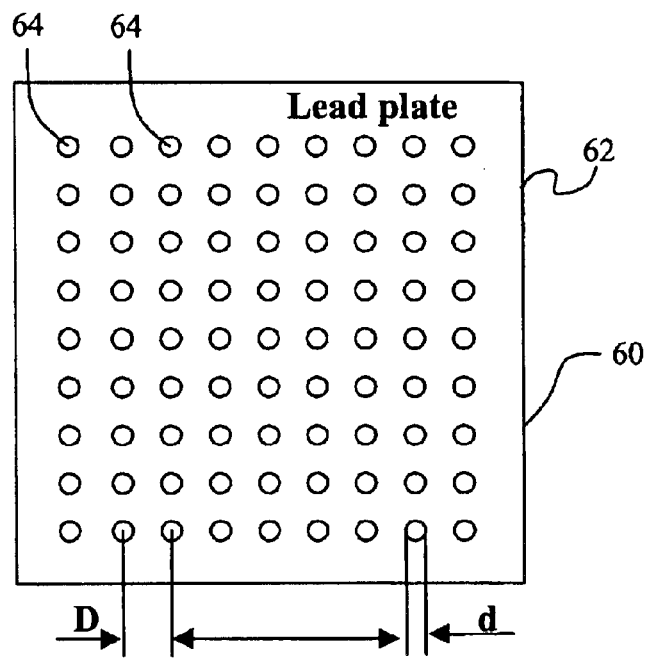
FIG. 3 illustrates a Bean Pass Array (BPA).

FIG. 3 illustrates a Beam Pass Array (BPA) 60 including a plate 62 containing a plurality of holes 64 of an adequate diameter to remove or reduce x-ray scatter interference. In an exemplary embodiment, plate 62 is fabricated from lead. In one embodiment, each hole 62 is circular and has a diameter (d) of about 1.5 mm, and spaced (D) from each other about 5 mm. Alternatively, holes 62 are a shape other than circular such as a square where d refers to the length of a side. In another embodiment, diameter (d) is between 1.2 mm and 1.8 mm and space (D) is between 4 mm and 6 mm. In yet another embodiment, d is between 1.0 mm and 2.0 mm and D between 3 mm and 7 mm.

Figure 4:
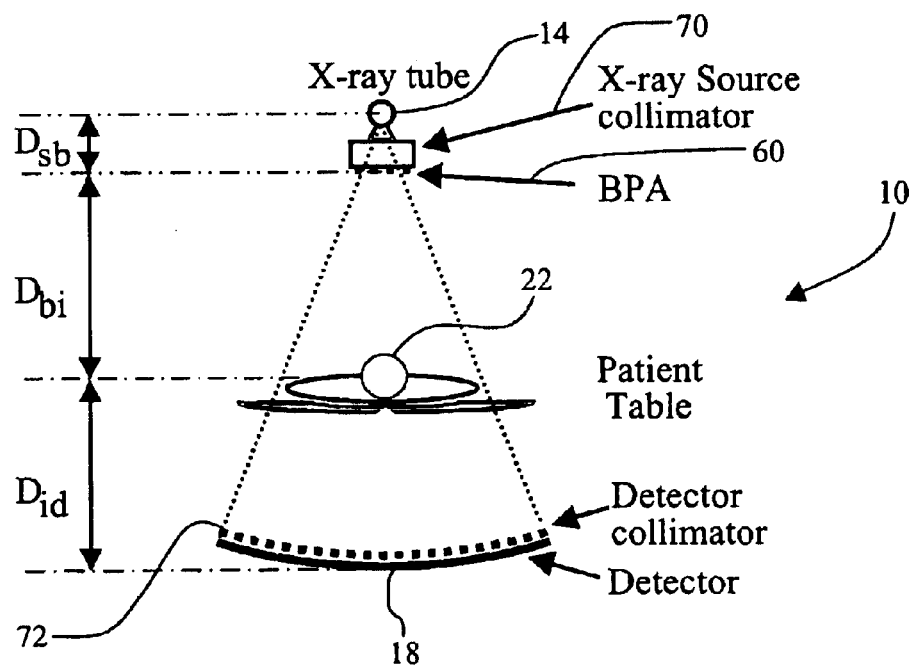
FIG. 4 illustrates the BPA shown in FIG. 3 installed in the CT system shown in FIG. 1.

FIG. 4 illustrates BPA 60 removably positioned between x-ray source 14 and detector 18 in system 10. System 10 also includes a source collimator 70 and a detector collimator 72. A distance between x-ray source 14 and BPA 60 is designated as $D_{sb}$. A distance between BPA 60 and the central axis of gantry 12 is designated $D_{bi}$. A distance between the central axis and detector 18 is designated as $D_{id}$.

In use, two projection images are acquired. $I_1(x,y)$ without BPA 60 placed between x-ray source 14 and object 22 to be imaged, and $I_2(x,y)$ with BPA 60 placed between source 14 and object 22, in which x-ray intensities at illuminated spots are exclusively formed by primary x-ray photons, because the diameter of holes is adequately small. Subtracting $I_2(x,y)$ from $I_1(x,y)$, one obtains $$I_\Delta(x,y)=I_1(x,y)-I_2(x,y) \quad (3)$$

Measuring $I_\Delta(x,y)$ at illuminated spots, one obtains $I_s(s_x, s_y)$, a sampled version of $I_s(x,y)$ $$I_s(s_x,s_y)=SS[I_\Delta(x,y)] \quad (4)$$

where the SS operator represents spatial sampling. Moreover, through spatial interpolation, such as linear or cubic B-spline interpolation, one can obtain an estimation of $I_s(x,y)$ $$\tilde{I}_s(x,y) = SI[I_s(s_x, s_y)] \quad (5)$$

where the operator SI represents the spatial interpolation. Eventually, one obtains an estimation of the primary image $$\tilde{I}_p(x,y) = I_1(x,y) - \tilde{I}_s(x,y) \quad (6)$$

in which x-ray scatter interference has been reduced or eliminated.

A projection image sequence $P_t(a_n;x,y)$ (n=1 ... N) is generated by consecutively acquiring x-ray projection images along an x-ray source trajectory, where $a_n$ represents the angular position of x-ray source. Similarly, $P_t(a_n;x,y)$ (n=1 ... N) can be decomposed into a primary image sequence and a scatter image sequence, wherein $$P_t(a_n;x,y) = P_p(a_n;x,y) + P_s(a_n;x,y) \quad (n=1 \ldots N)$$

According to the rationale elucidated above, two image sequences are acquired at each x-ray source position to obtain the primary image sequence $P_p(a_n;x,y)$ (n=1 ... N): (1) $P_1(a_n;x,y)$ (n=1 ... N) without a BPA; (2) $P_2(a_{n'};x,y)$ (n'=1 ... N') with a BPA placed between the x-ray source and the object. Ideally, $a_n$ should be equal to $a_{n'}$, but in reality $a_n \neq a_{n'}$, because the angular position of x-ray source 14 may not be the identical among different gantry rotations. In one embodiment, the angular misalignment is corrected because one can obtain another image sequence $\tilde{P}_1(a_{n'};x,y)$ (n'=1 ... N') that is aligned with $P_2(a_{n'};x,y)$ (n'=1 ... N') in angular x-ray source positions by angularly interpolating image sequence $P_1(a_n; x,y)$ (n=1 ... N), wherein $$\tilde{P}_1(a_{n'};x,y) = AI[P_1(a_n;x,y)](n'=1 \ldots N') \quad (8)$$

where the operator AI represents an angular (linear or cubic B-spline) interpolation.

Subsequently, $$P_\Delta(a_{n'};x,y) = \tilde{P}_1(a_{n'};x,y) - P_2(a_{n'};x,y) \quad (n'=1 \ldots N') \quad (9)$$

$$P_s(a_{n'};s_x, s_y) = SS[P_\Delta(a_{n'};x,y)](n'=1 \ldots N' \quad (10)$$

Again, through angular interpolation and spatial interpolation respectively, $$P_s(a_n;s_x,s_y) = AI[P_s(a_{n'};s_x,s_y)]\}(n=1 \ldots N) \quad (11)$$

$$\tilde{P}_s(a_n;x,y) = SI[\tilde{P}_s(a_n;s_x,s_y)](n=1 \ldots N) \quad (12)$$

one eventually obtains $$\tilde{P}_p(a_n;x,y) = P_1(a_n;x,y) - \tilde{P}_s(a_n;x,y) \quad (n=1 \ldots N) \quad (13)$$

Tomographic images in which x-ray scatter interference has been significantly reduced or almost eliminated are reconstructed from the image sequence $\tilde{P}_p(a_n;x,y)$ through various known CB reconstruction algorithms. Additionally, although the image sequence $P_1(a_n;x,y)$ (n=1 ... N) was angularly interpolated to obtain $\tilde{P}_1(a_n;x,y)$ (n'=1 ... N'), it is contemplated that $P_2(a_{n'};x,y)$ (n'=1 ... N') can be likewise angularly interpolated to angularly align the image sequences.

Typically, N'<<N due to an intensive angular correlation in the scatter image sequence. The diameter (d) of holes 64 are adjusted appropriately to achieve an accurate measurement, since a too big hole can be passed through by scattered x-ray photons, and a too small hole is subject to the interference caused by penumbra of primary photons. Meanwhile, the inter-distance of (D) of holes 64 are adjusted appropriately to achieve an accurate estimation of the image formed by scattered x-ray photons, because a too sparse array can degrade the estimation accuracy of the scattered image and a too dense array can result in unnecessary x-ray dose to a patient Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station.

The herein described methods and apparatus improves image quality in CB volumetric CT by reducing or eliminating interference caused by x-ray scatter, and improves image quality in CB volumetric CT by maintaining a DQE uniformity of x-ray detectors with large numbers of rows, e.g., above 64.

The herein described apparatus and methods combat x-ray scatter interference in CB volumetric CT, and are based upon x-ray scatter intensity sampling and image processing. The apparatus and methods are illustrated with reference to the figures which are intended to be illustrative rather than limiting. Accordingly, the spirit and scope of the invention are to be limited only by the terms of the appended claims.

What is claimed is:

1. A method comprising:
   scanning an object with a cone beam volumetric computed tomography (CBVCT) system with a beam pass array positioned between an x-ray source of the CBVCT system and the object to acquire scatter data;
   scanning the object with the CBVCT system without the beam pass array positioned between the x-ray source and the object to acquire image data; and
   correcting the image data using the scatter data.

2. A method in accordance with claim 1 wherein said correcting comprises angularly interpolating at least one of the scatter data and the image data to correct for angular misalignment.

3. A method in accordance with claim 2 wherein said angularly interpolating comprises angularly interpolating the image data to correct for angular misalignment, said method further comprising angularly and spatially interpolating the scatter data to obtain a projection scatter estimate.

4. A method in accordance with claim 1 further comprising angularly and spatially interpolating the scatter data to obtain a projection scatter estimate.

5. A method in accordance with claim 4 wherein said correcting the image data comprises subtracting the projection scatter estimate from the image data on a pixel by pixel basis.

6. A method in accordance with claim 1 wherein said scanning an object with a cone beam volumetric computed tomography (CBVCT) system with a beam pass array positioned between an x-ray source of the CBVCT system and the object to acquire scatter data comprises scanning an object with a cone beam volumetric computed tomography (CBVCT) system with a beam pass array positioned between an x-ray source of the CBVCT system, wherein the beam pass array comprises a plate with a plurality of openings therethrough, each opening spaced from other openings by at least 3 mm.

7. A method in accordance with claim 1 wherein said scanning an object with a cone beam volumetric computed tomography (CBVCT) system with a beam pass array positioned between an x-ray source of the CBVCT system and the object to acquire scatter data comprises scanning an object with a cone beam volumetric computed tomography (CBVCT) system with a beam pass array positioned between an x-ray source of the CBVCT system, wherein the beam pass array comprises a plate with a plurality of circular openings therethrough, each opening having a diameter of at least 1 mm.

8. A method in accordance with claim 7 wherein said wherein the beam pass array comprises a plate with a plurality of circular openings therethrough, each opening having a diameter of at least 1 mm comprises scanning an object with a cone beam volumetric computed tomography (CBVCT) system with a beam pass array positioned between an x-ray source of the CBVCT system, wherein the beam pass array comprises a plate with a plurality of circular openings therethrough, each opening having a diameter of at most 2 mm.

9. A method in accordance with claim 8 wherein said scanning an object with a cone beam volumetric computed tomography (CBVCT) system with a beam pass array positioned between an x-ray source of the CBVCT system and the object to acquire scatter data comprises scanning an object with a cone beam volumetric computed tomography (CBVCT) system with a beam pass array positioned between an x-ray source of the CBVCT system, wherein the beam pass array comprises a plate with a plurality of openings therethrough, each opening spaced from other openings by at least 3 mm.

10. A cone beam volumetric computed tomography system comprising:
   an x-ray source;
   a detector positioned to receive x-rays emitted from said source; and
   a beam pass array removably positioned between said source and said detector.

11. A system according to claim 10 wherein said beam pass array comprises a plate with a plurality of openings therethrough, each opening spaced from other openings by at least 3 mm.

12. A system according to claim 11 wherein said opening comprise a plurality of circular openings, each said circular opening having a diameter of at least 1 mm.

13. A system according to claim 12 wherein each said circular opening having a diameter of at most 2 mm.

14. A system according to claim 13 wherein each said circular opening having a diameter of approximately 1.5 mm.

15. A system according to claim 10 further comprising a computer operationally coupled to said detector, said computer configured to:
   receive scatter data from a scan of an object;
   receive image data from a scan the object with the beam pass array removed; and
   correct the image data using the scatter data.

16. A system according to claim 15 wherein said computer further configured to angularly interpolate at least one of the scatter data and the image data to correct for angular misalignment.

17. A system according to claim 16 wherein said computer further configured to angularly and spatially interpolate the scatter data to obtain a projection scatter estimate.

18. A system according to claim 16 wherein said computer further configured to correct the image data by subtracting the projection scatter estimate from the image data on a pixel by pixel basis.

19. A computer readable medium encoded with a program configured to instruct a computer to:
   receive scatter data from a cone beam scan of an object with a beam pass array present;
   receive image data from a cone beam scan the object without the beam pass array present; and
   correct the image data using the scatter data.

20. A medium in accordance with claim 19 wherein said program further configured to instruct the computer to angularly and spatially interpolate the scatter data to obtain a projection scatter estimate.

21. A medium in accordance with claim 17 wherein said program further configured to instruct the computer to angularly interpolate the image data to correct for angular misalignment.

* * * * *